United States Patent
Gobron

(10) Patent No.: US 7,553,166 B2
(45) Date of Patent: Jun. 30, 2009

(54) ELECTRICAL CONNECTOR FOR CONNECTING A PLURALITY OF PRINTED CIRCUITS

(75) Inventor: Stephane Gobron, Carlsbad, CA (US)

(73) Assignee: Lifesync Corporation, Fort Lauderdale, FL (US)

(*) Notice: Subject to any disclaimer, the term of this patent is extended or adjusted under 35 U.S.C. 154(b) by 38 days.

(21) Appl. No.: 11/703,928

(22) Filed: Feb. 8, 2007
(Under 37 CFR 1.47)

(65) Prior Publication Data

US 2007/0184682 A1 Aug. 9, 2007

Related U.S. Application Data

(60) Provisional application No. 60/771,742, filed on Feb. 9, 2006.

(51) Int. Cl.
*H01R 12/00* (2006.01)
*H05K 1/00* (2006.01)

(52) U.S. Cl. ............... 439/67; 439/287; 439/909

(58) Field of Classification Search .......... 439/67, 439/74, 65, 909, 883, 777, 257
See application file for complete search history.

(56) References Cited

U.S. PATENT DOCUMENTS

| | | | |
|---|---|---|---|
| 4,328,814 A | 5/1982 | Arkans | |
| 4,490,005 A | 12/1984 | Hovey | |
| 4,522,211 A | 6/1985 | Bare et al. | |
| 4,583,549 A | 4/1986 | Manoli | |
| 4,702,256 A | 10/1987 | Robinson et al. | |
| 4,797,125 A | 1/1989 | Malana | |
| 4,957,109 A | 9/1990 | Groeger et al. | |
| 4,978,306 A | 12/1990 | Robb | |
| 5,018,980 A | 5/1991 | Robb | |
| 5,326,272 A | 7/1994 | Harhen et al. | |
| 5,355,883 A | 10/1994 | Ascher | |
| 5,454,739 A | 10/1995 | Strand | |
| 5,484,294 A * | 1/1996 | Sobhani ............... 439/21 |
| 5,551,882 A | 9/1996 | Whiteman, Jr. et al. | |
| 5,588,843 A | 12/1996 | Sobhani | |
| 5,626,135 A | 5/1997 | Sanfilippo | |
| 5,692,908 A | 12/1997 | Fehlmann et al. | |
| 5,730,126 A | 3/1998 | Kantner et al. | |
| 5,788,633 A | 8/1998 | Mahoney | |
| 5,862,803 A | 1/1999 | Besson et al. | |
| 5,957,854 A | 9/1999 | Besson et al. | |
| 5,990,772 A | 11/1999 | Van Zeeland | |
| 6,132,219 A | 10/2000 | Sobhani et al. | |
| 6,223,088 B1 | 4/2001 | Scharnberg et al. | |
| 6,289,238 B1 | 9/2001 | Besson et al. | |
| 6,441,747 B1 | 8/2002 | Khair et al. | |
| 6,475,153 B1 | 11/2002 | Khair et al. | |
| 6,487,430 B1 | 11/2002 | Henderson et al. | |

(Continued)

*Primary Examiner*—Javaid Nasri
(74) *Attorney, Agent, or Firm*—Darby & Darby PC

(57) ABSTRACT

The present invention comprises an inexpensive and simple means for electrically and mechanically connecting a plurality of printed circuits together. The present invention also comprised embodiments where the printed circuits can be moved relative to each other without breaking the electrical contact between them. Yet another embodiment contemplates a means for joining two linear printed circuits to make a longer circuit. In yet another embodiment, the printed circuits and connections are used to make an inexpensive, reliable electrical harness for contacting a patient-worn sensor to a patient monitor such as an ECG monitor.

16 Claims, 21 Drawing Sheets

U.S. PATENT DOCUMENTS

| | | |
|---|---|---|
| 6,496,705 B1 | 12/2002 | Ng et al. |
| 6,533,729 B1 | 3/2003 | Khair et al. |
| 6,577,893 B1 | 6/2003 | Besson et al. |
| 6,611,705 B2 | 8/2003 | Hopman et al. |
| 6,612,848 B1 | 9/2003 | Brundage |
| D492,248 S | 6/2004 | Gregory et al. |
| D499,488 S | 12/2004 | Chastain et al. |
| 6,897,788 B2 | 5/2005 | Khair et al. |
| 6,987,965 B2 | 1/2006 | Ng et al. |
| 2003/0105403 A1 | 6/2003 | Istvan et al. |
| 2003/0160669 A1 | 8/2003 | Trandafir |
| 2003/0199777 A1 | 10/2003 | Hopman et al. |
| 2004/0015058 A1 | 1/2004 | Besson et al. |
| 2004/0019288 A1 | 1/2004 | Kinast |
| 2004/0072475 A1 | 4/2004 | Istvan et al. |
| 2004/0073127 A1 | 4/2004 | Istvan et al. |
| 2004/0127802 A1 | 7/2004 | Istvan et al. |
| 2004/0176675 A1 | 9/2004 | Rice et al. |
| 2004/0186358 A1 | 9/2004 | Chernow et al. |
| 2005/0251002 A1 | 11/2005 | Istvan et al. |
| 2005/0251003 A1 | 11/2005 | Istvan et al. |
| 2005/0251004 A1 | 11/2005 | Istvan et al. |
| 2006/0058017 A1 | 3/2006 | Ng et al. |

* cited by examiner

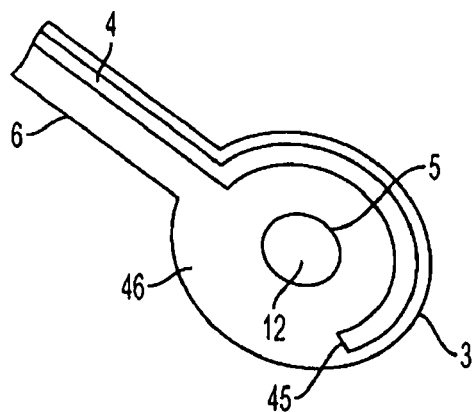
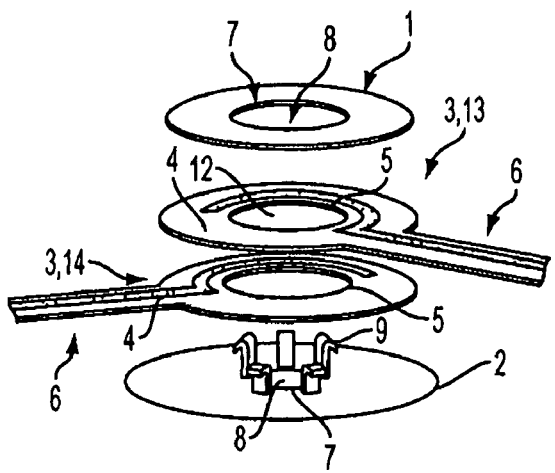
FIG. 1          FIG. 2
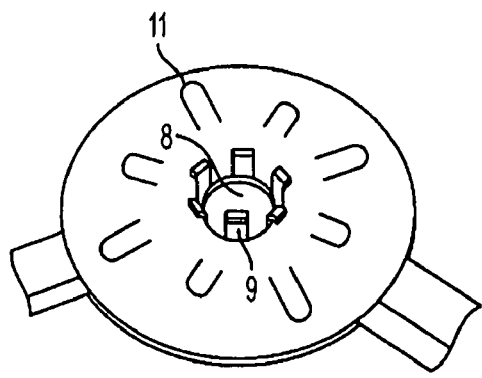
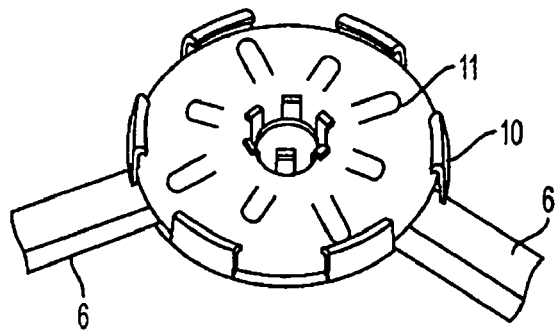
FIG. 3          FIG. 4

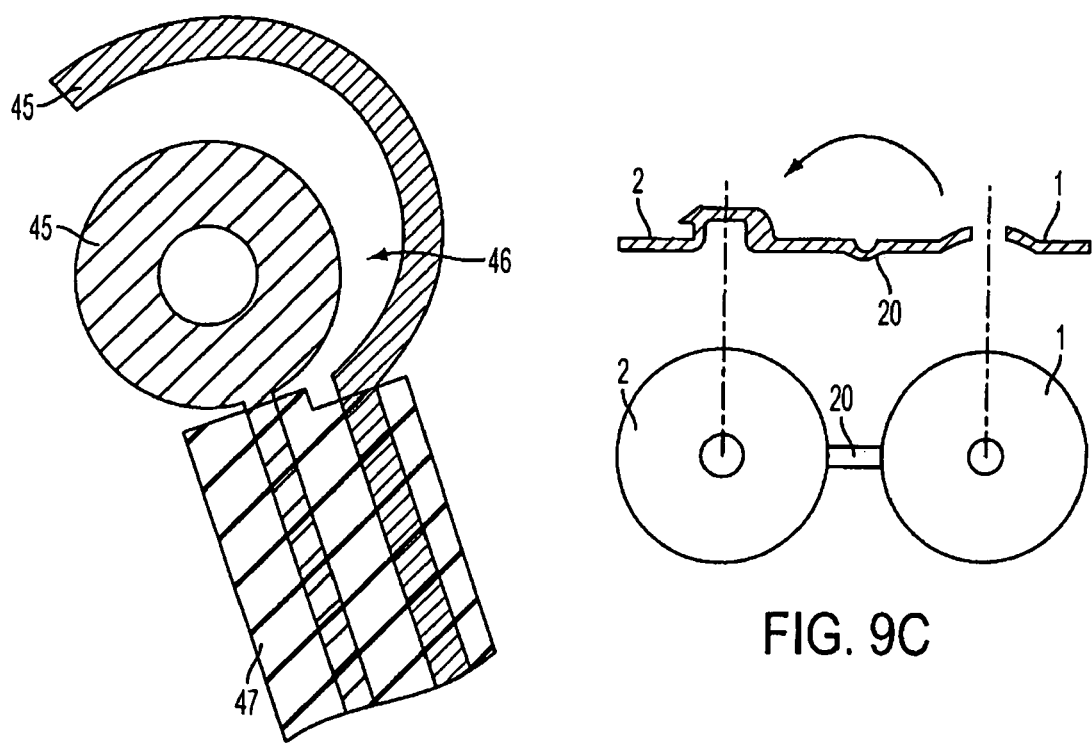
FIG. 9A
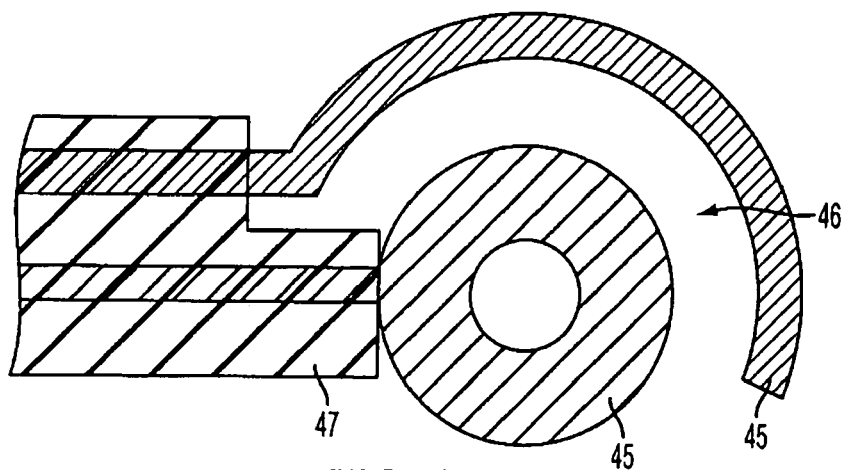
FIG. 9B
FIG. 9C

ELECTRICAL CONNECTOR FOR CONNECTING A PLURALITY OF PRINTED CIRCUITS

This application claims priority to corresponding U.S. Provisional Application No. 60/771,742, filed on Feb. 9, 2006, which incorporates U.S. application Ser. No. 10/439,356, filed on May 16, 2003, U.S. application Ser. No. 11/077,934, filed on Mar. 11, 2005, U.S. application Ser. No. 11/105,230, filed on Apr. 12, 2005, U.S. application Ser. No. 11/105,231, filed on Apr. 12, 2005, U.S. application Ser. No. 11/105,232, filed on Apr. 12, 2005, U.S. application Ser. No. 09/998,733, filed on Nov. 30, 2001, and U.S. application Ser. No. 09/908,509, filed on Jul. 17, 2001, now U.S. Pat. No. 6,611,705, the disclosures and contents of which are expressly incorporated herein by reference.

BACKGROUND OF THE INVENTION

Flexible circuits are widely used in the electrical arts to make electrical connections between separate pieces of hardware. Such circuits are generally made from an electrically inert substrate such as polyester film upon which are printed electrically conductive traces. The traces are printed with conductive inks containing copper, silver, gold, carbon or any electrically conductive material, generally in an epoxy base. The cost of using flexible circuits depends on the distance and shape between the circuits to be connected. Flexible circuits are made using polyester film substrates of a fixed width and length. The circuits are patterned onto the substrate in the most efficient manner possible to reduce waste. Circuits that require turns or very long segments of straight lengths often waste significant material due to limitations on how the patterns can be laid out to maximize the use of material.

Using current technology, substrate waste can be reduced by using hard connectors between discrete sections of flexible circuits. While such approach reduces the amount of substrate used, using hard connectors between discrete sections of circuits adds cost and complexity.

There is a need in the electrical arts for a means to join printed circuits including both flexible and relatively inflexible circuits without a need for hard connectors.

Additionally, there is a need in the art for connections between printed circuits which can be moved to permit different configurations of the circuit. This need frequently arises when the electrical components to be connected need to be placed at varying distances from each other based on the needs of the user.

There is a specific application for the present technology in the medical field where patients are monitored via electrodes placed on the skin. Electrodes or other electrical sensing equipment have long been used in the medical field for attachment to a human being or otherwise living organism in order to monitor physiological functions such as the electrical signals of the heart. The electrodes take on several forms and must in some way be electrically connected to a device suitable for storing and oftentimes, for processing and analyzing the electrical signals gathered from the sensing equipment.

Typically, individual electrodes are connected to the monitoring device by separate electrical leads. A flat sheet, tab-like electrode is often connected to the lead wire using an alligator-type clip formed by two jaws which clamp together to secure the lead wire to the electrode. The jaws often contain various mechanisms for crimping the electrode surface for better connection. However, such a configuration restrictively grips the electrode thereby preventing any movement between the lead wire and the electrode. Such a limitation leads to significant cable strain along the lead wire and the need to disengage and reattach the lead wires whenever the subject being monitored moves or the monitoring equipment is moved in a different orientation. Described are several connections to tab-like electrodes which provide for some rotational movement between the electrode and lead wire. For example, the electrode can include a hole whereby a protruding member located on the surface of one of the jaws of the alligator clip is inserted through the hole and when the two jaws are clamped together, structurally mates with the opposite jaw. Therefore, the electrode is not restrictively gripped in place but rather can be rotated around the protruding member.

Where stud-type electrodes are used, typically an individual lead wire is connected to the stud portion of the electrode using an alligator-type clip or a snap-type connector whereby the stud portion is inserted into a tight aperture formed in the connector such that the stud is snapped into connection. Both of these configurations ordinarily only serve to connect a single lead wire to an electrode and therefore require that each electrode be individually connected to a monitoring device. Many applications require that more than one electrode be used in sensing a physiological function and often, it is not practical to require each electrode be individually connected. The use of individual leads risks entanglement and confusion between the wires. Although a connector which may be rotated with respect to the electrode is much more easily adapted to the shape of a stud-type electrode in comparison to a tab-style electrode, the use of a plurality of individual wires to attach a subject to a monitoring device severely limits the mobility of the subject being monitored. The comfort of the subject is compromised and the ability to monitor a physiological function while the subject is active is nearly impossible.

Chest assemblies have been disclosed whereby a plurality of electrode connections or electrodes are integrated into a single, flexible chest patch. The electrode connections are typically in the form of slots or holes integrated into the surface of the chest patch such that the slots or holes are snap-fitted onto the protruding member of stud-type electrodes. The electrical pathways leading away from the electrode connections are typically circuit traces printed along the patch substrate which terminate at a single terminal on an edge of the patch such that the traces are in close proximity to one another. Various means are used to connect the terminal edge to a monitoring device using a single connection. Therefore, a plurality of individually connected electrode leads is eliminated. However, a single wire connection between the terminal edge and the monitoring device still requires that the subject be tethered such that mobility and comfort are still restricted. Also, due to the fact that the electrode connections are integrated along a single chest patch, the placement of the electrodes upon the subject being monitored is fixed or substantially limited in order to correspond to the electrode connections defined in the chest patch. Therefore, only one configuration is possible. Although limiting electrode placement may be beneficial in avoiding improper placement, the benefit is limited as the chest patch must still be properly placed on the chest in the first instance. Also, the chest patches are ordinarily composed of a flexible material such as a plastic derivative in order for the patch to conform well to the variable surface of the chest for a good connection. Therefore, the chest patch must be packaged assembled in its entirety and great care must be taken so that the patch is not bent or otherwise problematically shaped as it is easily pliable.

Other chest assemblies with integrated electrode connections have eliminated the use of a single wire connection to a separate monitoring device and replaced it with data processing means that are integrated into the chest patch. The chest patch is either made completely self-sufficient or has an antenna included for wireless transmission to a separate monitoring device. Although such a configuration provides much greater comfort and mobility to the subject being monitored, the costs of such an integrated chest patch are much higher and thus would not be disposable. Where the chest assemblies will have a high frequency of use, a disposable component is much more desirable than a costly device which needs to be cleaned after each use.

These as well as other novel advantages, details, embodiments, features, and objects of the present invention will be apparent to those skilled in the art from the following detailed description of the invention, the attached claims and accompanying drawings, listed herein below which are useful in explaining the invention.

It is an object of this invention to provide a simple, easily connected and disconnected electrical connector which can be used to connect one or more flexible, printed circuit traces originating from separate electronic devices to a stud-type electrode. Such a connection may then be used as an integrated electrode connector in a chest assembly whereby the flexible, printed circuit traces originate from other integrated electrode connections along the length of the chest assembly. Therefore individual, multiple lead wire connections to the electrodes are eliminated and the comfort and mobility of the subject being monitored is maintained. One or more printed circuit traces terminate onto flexible circuit ends that each contain a centering axis whereby an aperture is formed. The ends of the circuit traces form an annular shape that is concentric to the center aperture. The connector consists of a top and bottom part, either separated or connected by a single living hinge, both containing a centering axis whereby an aperture is formed. The top and bottom parts are constructed so as to have a mating mechanism along the circumference of the inner aperture and/or along their outer edges such that they may be snap-fitted into connection with one another. The circuit ends are overlapped upon one another such that the printed circuit traces on each circuit end are in direct face-to-face electrical contact with one another. The center apertures of the stacked circuits are aligned with the center apertures of the top and bottom parts such that when the top and bottom parts are snap-fitted together, the stacked circuits are secured between the two parts. The snap-fit is easily connected and disconnected thereby reducing the chest assembly to multiple modular parts which are more easily manufactured and packaged in comparison to one unit. The protruding member of a stud-type electrode is inserted through the center aperture of the connector so as to electrically connect the printed circuit traces to the electrode.

It is a further object of this invention to provide a simple electrical connector that can be used to connect one or more flexible, printed circuit traces originating from separate electronic devices to a stud-type electrode such that each connected circuit may rotate freely about its centering axis and still maintain electrical contact with the overlapping circuits and the electrode. The ability to adjust the flexible circuits angularly with respect to one another allows for freedom of movement and placement of the electrode connections upon the chest that could not be achieved where the electrode connections are fixed in place on a single chest patch. Although the circuit ends are pressed into overlapping contact between the two flat, top and bottom surfaces of the connector and are held in place by a snap-fit mating mechanism at the aperture running through the centering axis of the connector, the circuits are not pressed so tightly together that they cannot be rotated easily. Also, although the circuit ends are held in place by a snap-fit mating mechanism at their centering axis, this snap-fit only serves to connect the top and bottom surfaces of the connector and to align the centering axes of the connector body and the circuit ends without restricting the rotation of the circuit ends.

It is a further object of this invention to provide a means for switching the connector between an "On" and "Off" position. The length of the annular printed circuit traces may be varied such that there are areas of angular rotation at which the annular traces of the overlapping circuits are no longer overlapping and therefore, are no longer in electrical connection placing the connector into an "Off" position.

It is a further object of this invention to provide several means for limiting the rotational movement about the centering axis of the circuit ends in applications where such a restriction provides an advantage. For example, the snap-fit mechanism that connects the top and bottom surfaces of the connector may be placed at the outer edge of the surfaces, either along the entire edge or intermittently, so as to prevent the circuit ends from traversing a complete rotational path about the circumference of the connector body. Also, a second hole may be incorporated into the connector such that insertion of a pin into the hole restricts the rotation of the circuit ends.

It is a further object of this invention that the described electrical connector be disposable.

BRIEF DESCRIPTION OF THE DRAWINGS

The foregoing aspects and many of the advantages of the present invention will become readily appreciated by reference to the following detailed description of the preferred embodiment, when taken in conjunction with the accompanying drawings, wherein:

FIG. 1 shows a mating end of a membrane circuit having a plurality of silver traces.

FIG. 2 shows an exploded view of the articulated connector assembly.

FIG. 3 shows the assembled connector.

FIG. 4 shows the connector with the outer snap assembly in place.

FIGS. 9A and 9B show the bottom and top circuit membranes respectively, with insulation cut away to allow electrical contact between the two membranes.

FIG. 9C shows a means of connecting circuits using a living hinge.

DETAILED DESCRIPTION

The present invention is an articulated electrical connector used to provide an electrical connection between printed circuits. The circuits may be flexible, semi-flexible or rigid circuits. The connection may be made between two discrete parts or may be used to connect different sections of the same circuit.

Figure 12A:
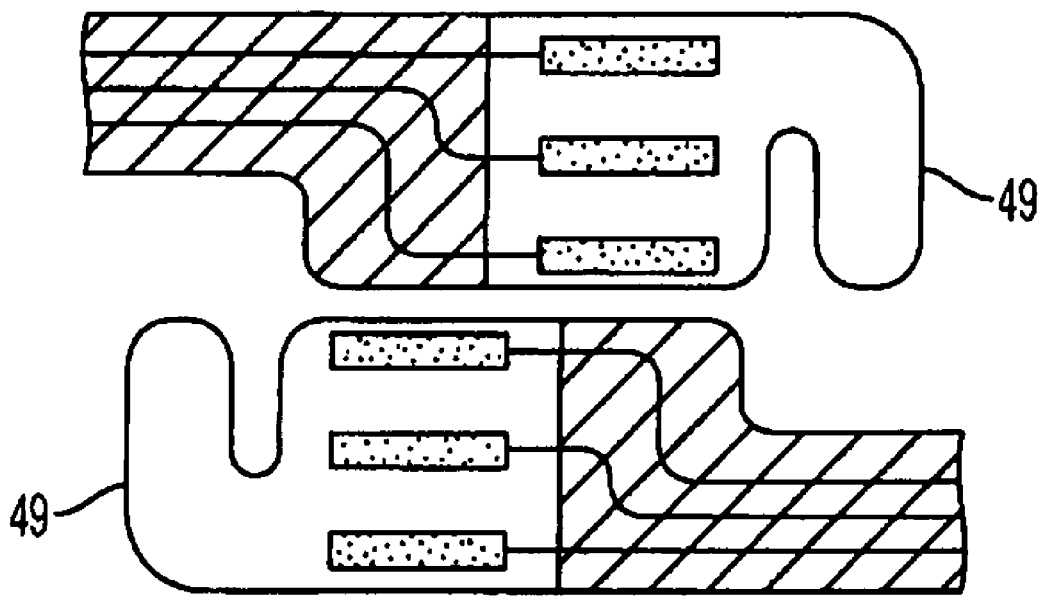
FIG. 12A shows a means of connecting circuits using matching hooks.
Figure 12B:
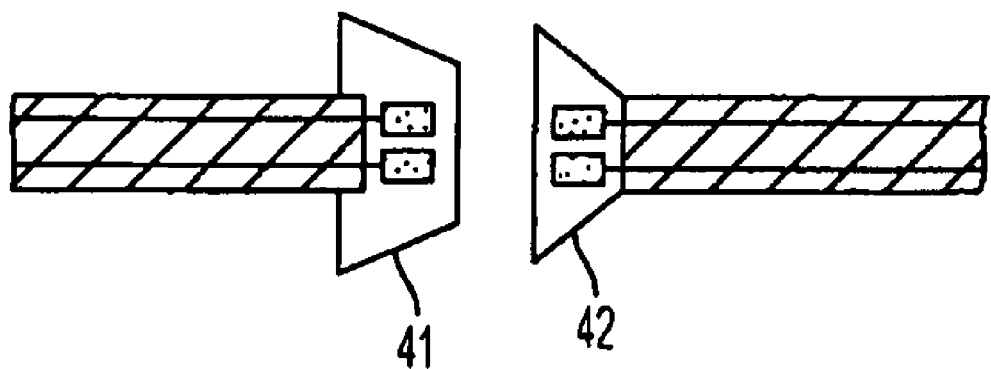
FIG. 12B shows a means of connecting circuits using friction/snap fit male and female connectors.

As shown in FIG. 1, at its simplest, the connector is nothing more than two or more of the illustrated exposed conductors 45 on a non-conductive backing 46 which are mated together and fastened to complete the connection. As shown in FIGS. 9A and 9B, the circuits may or may not have insulation 47 covering the traces in regions where they do not meet. Suitable fasteners include conductive and non-conductive adhesives, tapes, rivets, clips, clamps, interlocking fit, friction fit, or outer or intermediate housings or any suitable means to hold the two or more circuits together as may be required to maintain or prevent electrical contact as required by the particular circuit. For example, in one embodiment shown in FIG. 12A, the two or more circuits may have matching hooks 49 at the end of each circuit in order to connect the two or more circuits. In yet another embodiment, the circuit can be joined by making the connections self-locking. As shown in FIG. 12B, the mating circuit ends may be designed as mating male 41 and female 42. The male circuit 41 is shaped such that it is slightly larger than the opening of the female circuit but still capable of being inserted. Upon insertion, tangs or other protrusions on the male end engage with openings on the female circuit to prevent separation.

Figure 11A:
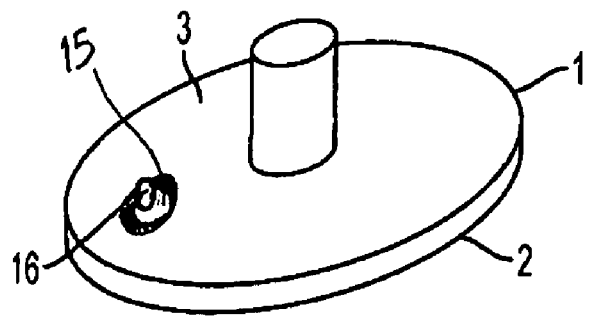
FIG. 11A shows the pin used on the snap component of the connector to limit rotation of the one or more articulated circuits.
Figure 11B:
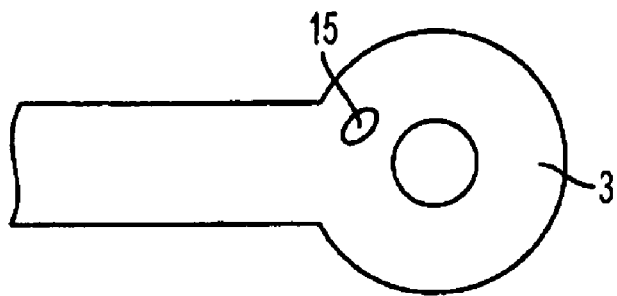
FIGS. 11B and 11C show the use of cutouts or holes on a membrane circuit to limit rotation of the one or more articulated circuits.
Figure 11C:
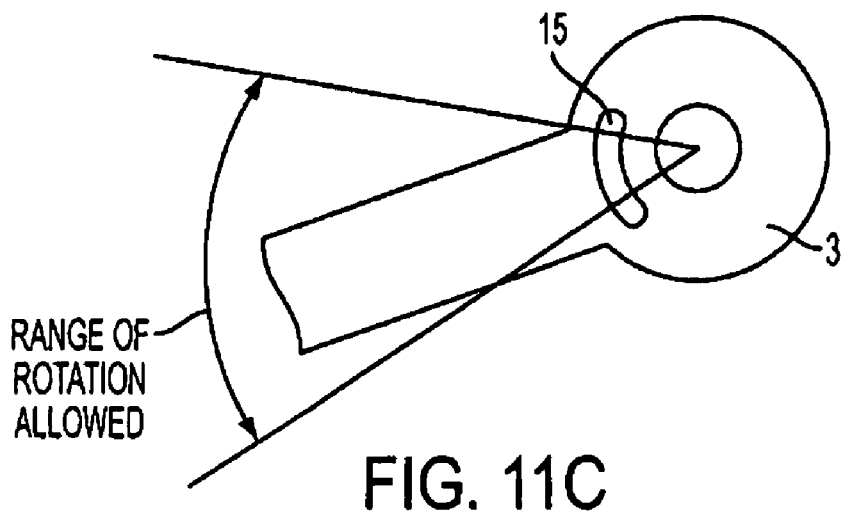

The connector may or may not allow motion of the connected circuits with respect to one another. Where desired, at least one electrical trace of each of two or more flexible, printed circuits can be assembled such that the connector allows each circuit a range of articulated, angular motion with respect to one another. Motion may be permitted by the use of snaps or rivets which hold the circuits together but still allow rotation about the axis of the snap or rivet. It will be apparent to one of reasonable skill in the art that some motion can be allowed by simply designing in a loose fit to the mating components. Respective motion of the connected circuits can be restricted by the choice of fastener at the connector. The use of adhesives or multiple points of mechanical fastening or tight tolerance enclosures or clamps will prevent motion at the joint. Motion can also be limited at the connector through the use of pegs and slots as shown in FIGS. 11A-C.

Referring to FIG. 2, one embodiment of the connector is comprised of a body that is separated into a top part 1, a bottom part 2, and at least one flexible, printed circuit end 3 [as shown in FIG. 1]. Top part 1 and bottom part 2 are preferably identical, circular, and composed of plastic. Top part 1 and bottom part 2 are flat and each contains a center axis 7. At each center axis 7 are apertures 8 such that when part 1 and part 2 are aligned in an overlapping configuration, apertures 8 are also aligned such that a separate electrically conducting member (not pictured) may be inserted through the aligned apertures 8. For example, an upstanding portion of an electrode may be inserted through apertures 8 such that the electrode is in electrical connection with the connector body. Apertures 8 are preferably circular in shape. Although, in a preferred embodiment, apertures 8 are placed at the centering axis 7, in no way does this description limit the placement of the apertures 8 at the centering axis as they may be placed anywhere along the surface of the connector body.

Figure 10:
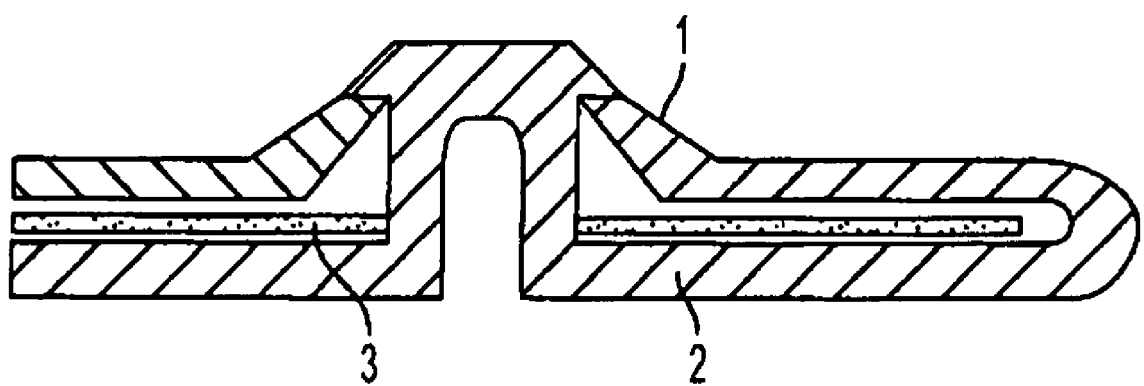
FIG. 10 is a cross-sectional view of the plastic snap assembly in place.

Top part 1 and bottom part 2 may contain a mating mechanism by which the two parts may be snap-fit together in a self-locking fashion [as shown in a cross-sectional view in FIG. 10]. As shown in FIGS. 2 and 3, either top part 1 or bottom part 2 may contain protrusions 9 located at centering axis 7 such that the protrusions line the outer perimeter of aperture 8. As shown in FIG. 3, the top and bottom parts of the connector are aligned and pressed together such that the protrusions 9 are snap-fitted into aperture 8 of the adjoining part such that the top and bottom parts are held together. The surfaces of the tips of protrusions 9 are angled such that parts 1 and 2 cannot freely come apart and are locked into place. Furthermore, as shown in FIG. 4, either top part 1 or bottom part 2 may contain protrusions 10 along its outer perimeter such that when parts 1 and 2 are aligned and pressed together, protrusions 10 snap about the outer edge of the adjoining part such that parts 1 and 2 are restrictively held together. The surfaces of the tips of protrusions 10 are similarly angled such that parts 1 and 2 cannot freely come apart and are locked into place. In an alternative embodiment as shown in FIG. 9C, top part 1 and bottom part 2 may be connected by a living hinge 20 such that the connector body is a single part rather than two separate parts. In order to connect the top and bottom parts, the hinge is collapsed in a closed position and the two parts are pressed together.

Figure 5:
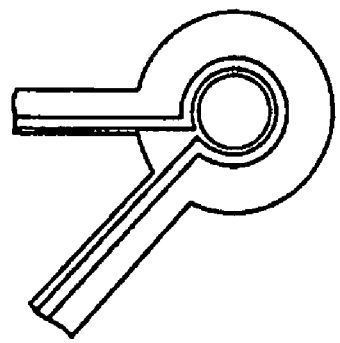
FIG. 5 shows the assembly in a folded configuration.
Figure 6:
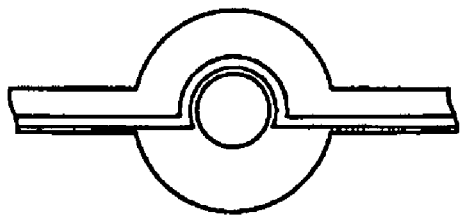
FIG. 6 shows the assembly in an extended configuration.

Referring back to FIG. 1, flexible circuit 6 is preferably composed of a non-conductive polyester support sheet which may contain one or more protruding silver traces 4 on one or both sides of the sheet. The plastic support sheet is insulated using a dielectric or some other type of material. Flexible circuit 6 terminates at circuit end 3, at which point each silver trace 4 terminates into an annular shape that is concentric about a centering axis 5. At the centering axis 5 is an aperture 12 such that when the connector is assembled, as shown in FIG. 2, aperture 12 is aligned with apertures 8 of top part 1 and bottom part 2 thereby forming an aperture throughout the entire assembly through which a separate electrically conducting member may be inserted. The silver traces 4 of circuit ends 3 are positioned such that where circuit ends 3 are aligned at their centering axis 5 in an overlapping fashion, traces 4 are also overlapping one another [as also shown in FIGS. 5 and 6]. Circuit end 3 is not covered by a dielectric or other insulating material 47 such that the annular silver traces 4 are left exposed [as shown in FIGS. 9A and 9B].

Figure 7:
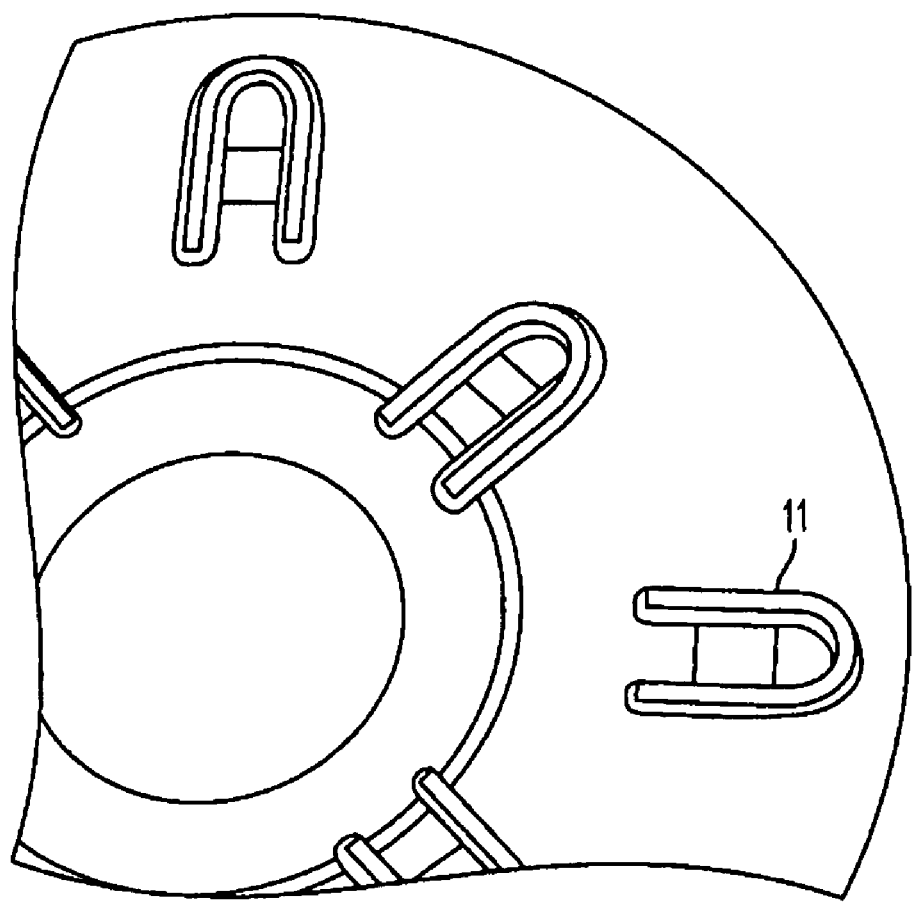
FIG. 7 shows the cantilever members for improving contact between the two or more articulated circuit membranes.
Figure 8A:
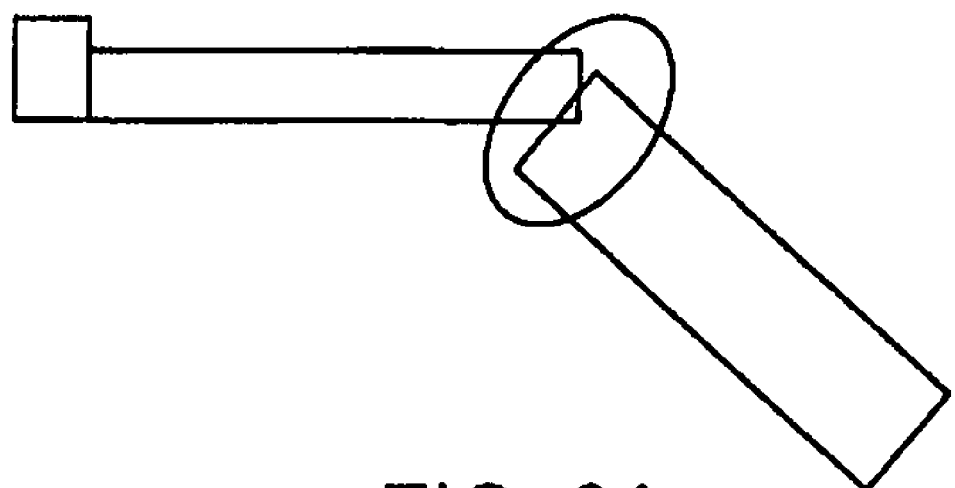
FIGS. 8A and 8B show the orientation of the top and bottom circuit membranes.
Figure 8B:
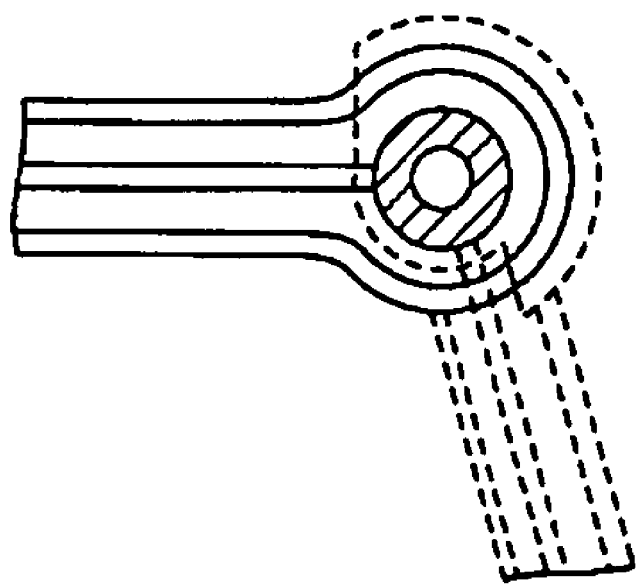

During assembly of the connector as illustrated in FIG. 2, the centering axis 7 of bottom part 2 is introduced into the bottom circuit end 14 such that the silver traces 4 of the bottom circuit end 14 face upward away from bottom part 2. The top circuit end 13 is introduced over bottom circuit 14 such that its silver traces 4 face the traces of the bottom circuit end 14 so as to create a face-to-face electrical connection between circuit ends 13 and 14. Top part 1 and bottom part 2 are then snap-fit together in order to complete the connector assembly. In order to connect circuit ends 13 and 14 to a separate electrically conducting member, the conducting member (not pictured) is inserted through the centering axis 5 of the connector assembly thereby in physical contact with the circuit ends. As shown in FIGS. 3, 4 and 7, cantilever members 11 or springs may be incorporated into the connector body on the surfaces of parts 1 or 2 in order to further press the circuit ends together for better electrical connection.

After assembled, the connector may allow for circuit ends 3 to have free, 360 degree rotation with respect to each other about the separate conducting member located at the centering axis 5 of the connector assembly. Alternatively, the circuit ends may be restricted by several mechanisms to only allow a certain degree of rotation or no rotation at all. As shown in FIG. 4, the outer protrusions 10 described above may restrict movement of the circuit ends 3 by preventing the flexible circuit 6 from traversing the entire circumference of the connector body as the protrusions serve as obstacles along the circumference path. Alternatively, as shown in FIGS. 11B-C, another hole 15 may be incorporated into the connector such that it protrudes through top part 1, bottom part 2, and circuit ends 3. As shown in FIG. 11A, a pin 16 is inserted into hole 15 so as to restrict movement of the circuit ends 3. As shown in FIGS. 11B-C, hole 15 may vary in size depending on the range of the angle of rotation that is desired. Movement may also be restricted by constructing aperture 8 to be a non-circular shape so that the inner protrusions 9 restrict any rotational movement about the centering axis 5.

Figure 13A:
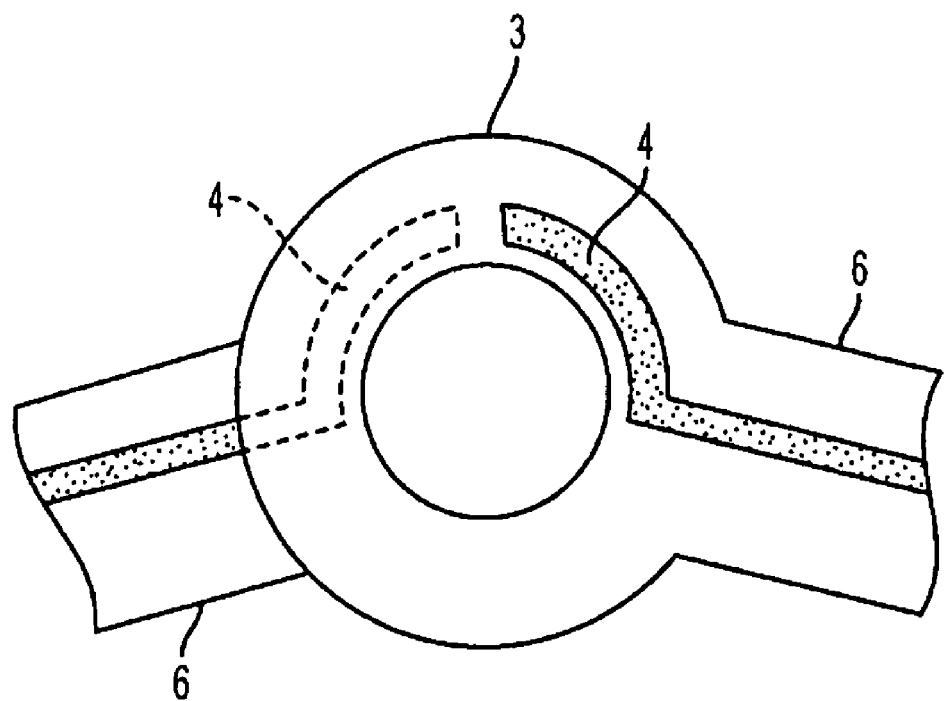
FIG. 13A shows two articulated circuit membranes in a non-activated or "Off" configuration.
Figure 13B:
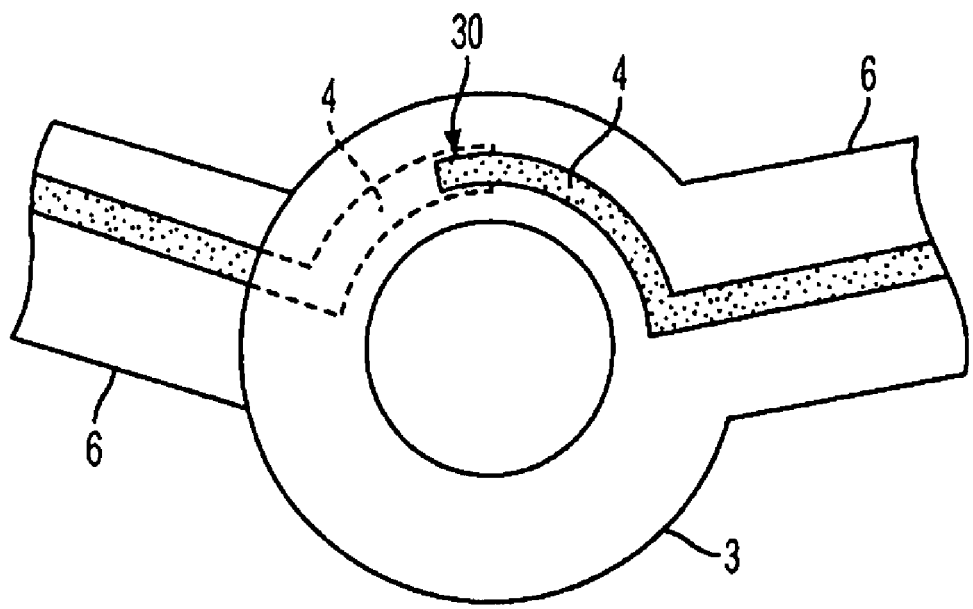
FIG. 13B shows two articulated membranes in an activated or "On" configuration.
Figure 13C:
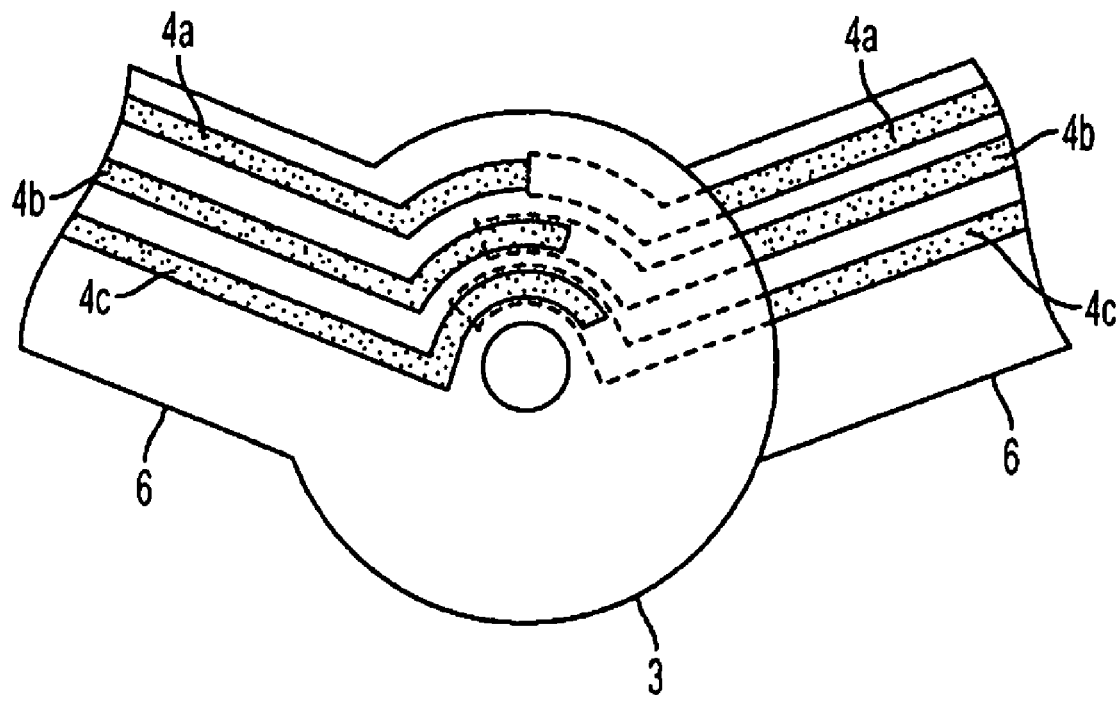
FIG. 13C shows how an articulated connection can be used to selectively activate one or more circuits.

As shown in FIGS. 13A-B, the connector may also act as an electrical switch whereby the electrical connection between the two or more circuit ends 3 of flexible circuits 6 may be turned "On" and "Off". Due to the fact that the electrical connection between the circuit ends 3 is made by overlapping their corresponding annular silver traces 4 such that the traces are in face-to-face direct contact, varying the lengths of the annular portions can create areas of angular rotation at which the traces are not in contact at all. Therefore, as shown in FIG. 13A, the traces may be separated and the circuit may be turned "Off" by rotating the circuit ends 3 to such an extent that the overlapping annular portions 4 are no longer in contact due to their limitations in length. In order to turn the electrical switch on as shown in FIG. 13B, the circuit ends 3 are again rotated in the opposite direction such that the annular portions 4 are in an overlapping configuration 30, thereby restoring electrical connection. Such an articulated connection can be used to selectively activate one or more circuits apart from all circuits that are present. For example, as shown in FIG. 13C, flexible circuits 6 contain three sets of corresponding annular traces 4a, 4b and 4c. The annular length of traces 4a is shorter than the annular length of traces 4b and 4c. The annular length of traces 4b is shorter than the annular length of traces 4c. Therefore, when flexible circuits 6 are rotated towards one another, corresponding traces 4c will overlap before traces 4b and 4a overlap such that an electrical connection is made between corresponding traces 4c before an electrical connection is made between the corresponding traces of 4a and the corresponding traces of 4b. In FIG. 13C, after advancing the angle of rotation to the point shown, only traces 4c and 4b are overlapping and therefore, only traces 4c and 4b are in electrical contact. As such, by varying the angle between circuit ends 3, one or more circuits can selectively be activated or switched "On" without simultaneously activating all circuits.

Figure 14:
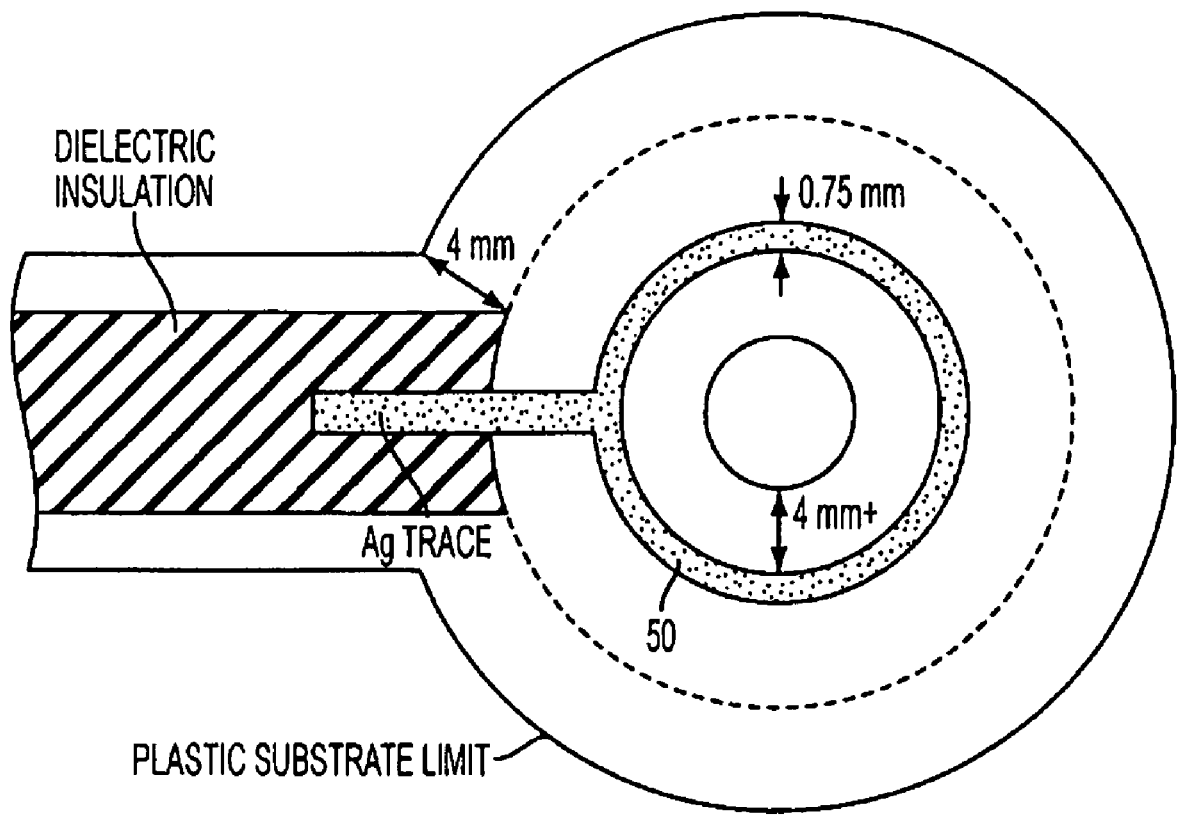
FIG. 14 shows the dimensions of the one or more traces on a circuit membrane and the degree of separation between the traces that is required to avoid arcing of the conducted electricity between the multiple traces.

When designing flexible traces and electrical arcing is a concern, any exposed traces should be of an appropriate thickness and have sufficient separation to safely conduct the intended current without jumping the gaps between traces. As shown in FIG. 14, with regards to an electrocardiogram (ECG) trace, the preferred thickness of the silver epoxy ink 50 is 0.75 mm and the traces should be approximately 4 mm apart.

As will be readily apparent to one of skill in the art, flat printed circuits can have any number of connections as contemplated by the present invention. Circuits can be arranged in series to create longer circuits from smaller pieces of material. Articulated and non-articulated connections can be made in the same circuit. The final intended circuit can be created from as many or as few parts as may be required to minimize wasted materials when printing the circuits.

Figure 15A:
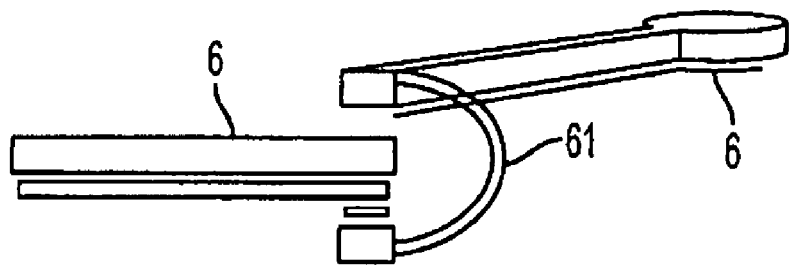
FIG. 15A shows how electrical contact can be made with a device on the opposite side of the conductive face of a circuit membrane using foldable flaps.
Figure 15B:
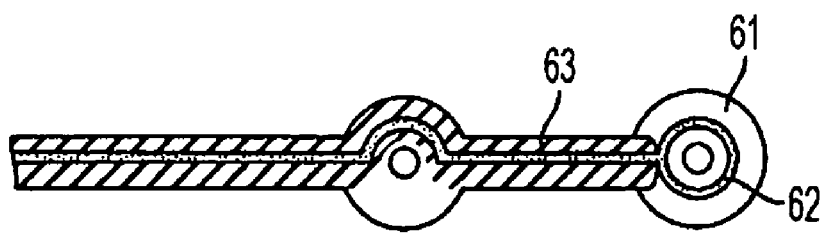
FIG. 15B shows the conductive and non-conductive (or insulated) surfaces of a main circuit membrane and a corresponding flap.
Figure 15C:
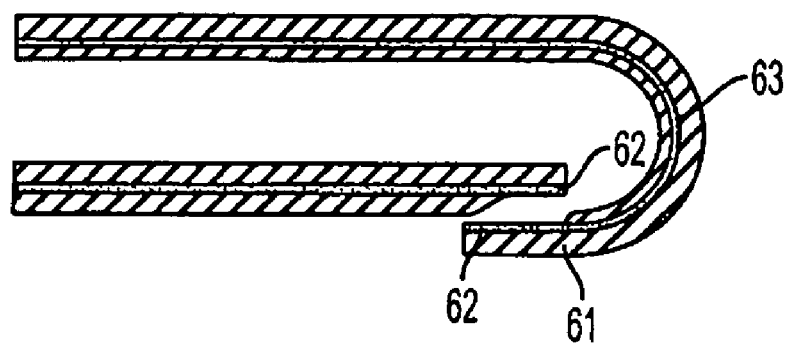
FIG. 15C shows a cross-section of the contact surfaces of the main circuit membrane, a folded-over flap and a second flexible circuit.

When using articulated connections, the traces on the joining circuits must face each other for electrical contact to occur. This presents a problem when the electrical contact must occur on the face of the end of a circuit that the circuit. However, such step requires additional effort in manufacturing. is opposite the side of the trace. In some instances it may be possible to remove portions of the substrate to expose the trace on the desired face of To reduce the number of manufacturing steps, it is desirable to create extensions or flaps 61 of the circuits 6 which can be doubled back in order that the electrical contact face and the traces are oriented such that they are face to face for electrical connection as show in FIG. 15A. These flaps are merely an extension of the electrical trace that extends beyond the intended circuit junction or connection. The extension terminates at a connection point having an exposed trace 62 [as shown in FIG. 15B]. FIG. 15B shows a linear flap showing regions of insulated traces 63 and non-insulated traces 62. In this embodiment the electrical connection is being made with the bottom side of the circuit. The trace, flap 61 is folded over the intended connection point such that it can make electrical contact with a conductive stud positioned on the substrate side of the circuit. FIG. 15C shows a cross-section of flap 61 in a folded-over configuration.

Figure 15D:
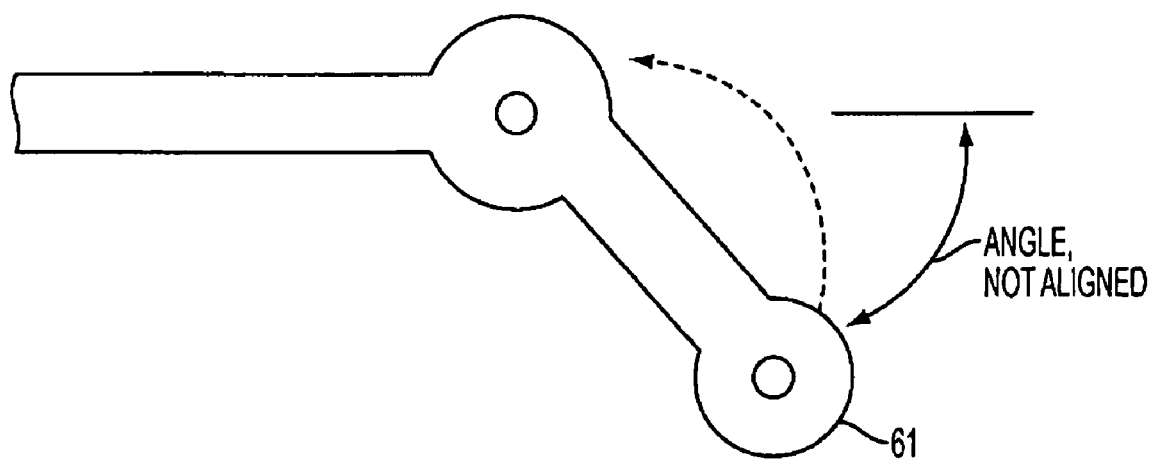
FIG. 15D shows the use of an offset, angled flap to avoid interference in a desired direction or to provide interference in a desired direction.

As shown in FIG. 15D, flap 61 can be arranged to any angle of orientation from the main body of the circuit in order to not restrict the types of configurations of the one or more circuits that may be used due to a restriction in the relative orientation of the flap connection. The orientation of the flap may be used to allow for movement in a desired direction or prevent movement in an undesired direction.

Figure 15E:
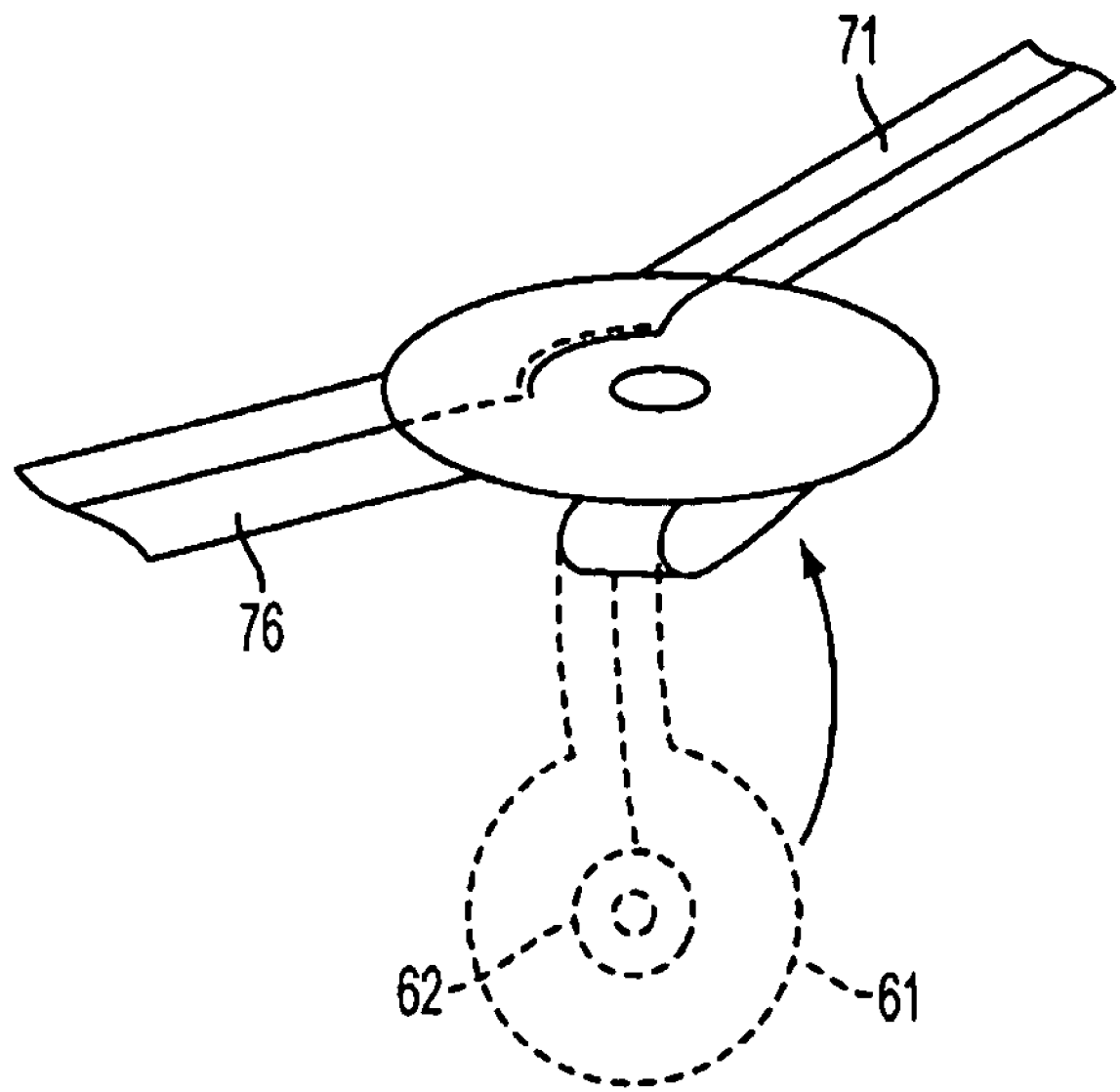
FIG. 15E shows a completed connection wherein the configuration is able to achieve a linear formation.

FIG. 15E shows the configuration of the present embodiment when incorporated into an ECG lead wire. In this embodiment, flexible circuit 71 having flap 61, is printed in one piece and has a plurality of extensions [for example, shown as a singular extension 76 in FIG. 15E] that may correspond to the conventional ECG anatomical positions of right arm, left arm, right leg, left leg and reference ground.

Figure 17A:
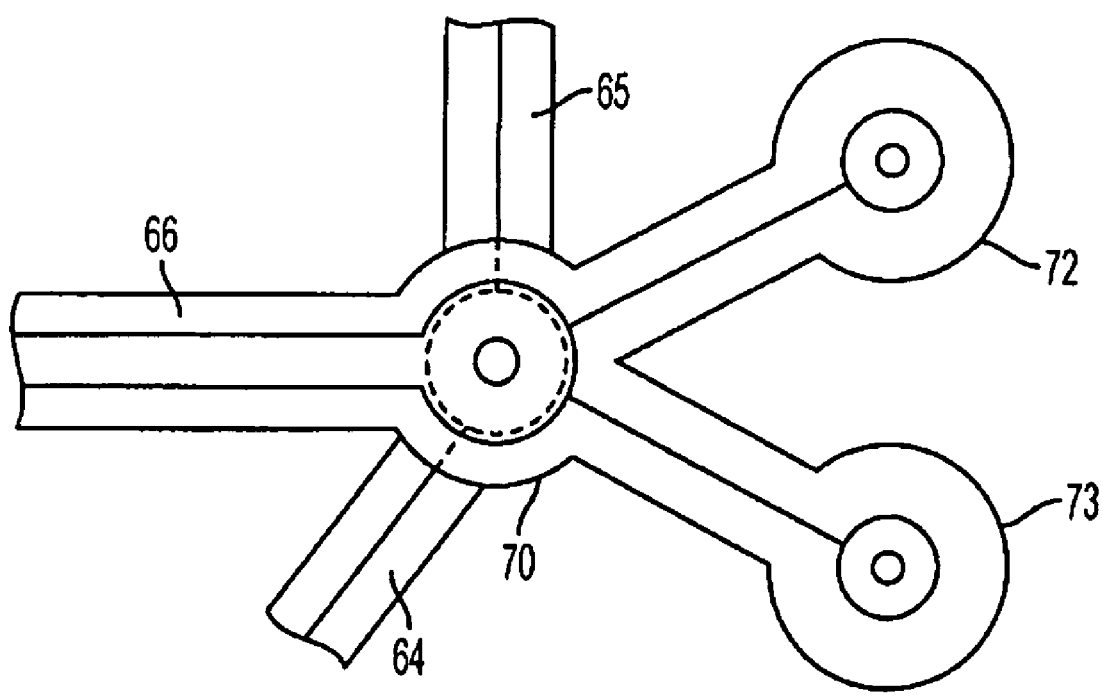
FIG. 17A demonstrates an unassembled circuit having dual articulations about a common axis.
Figure 17B:
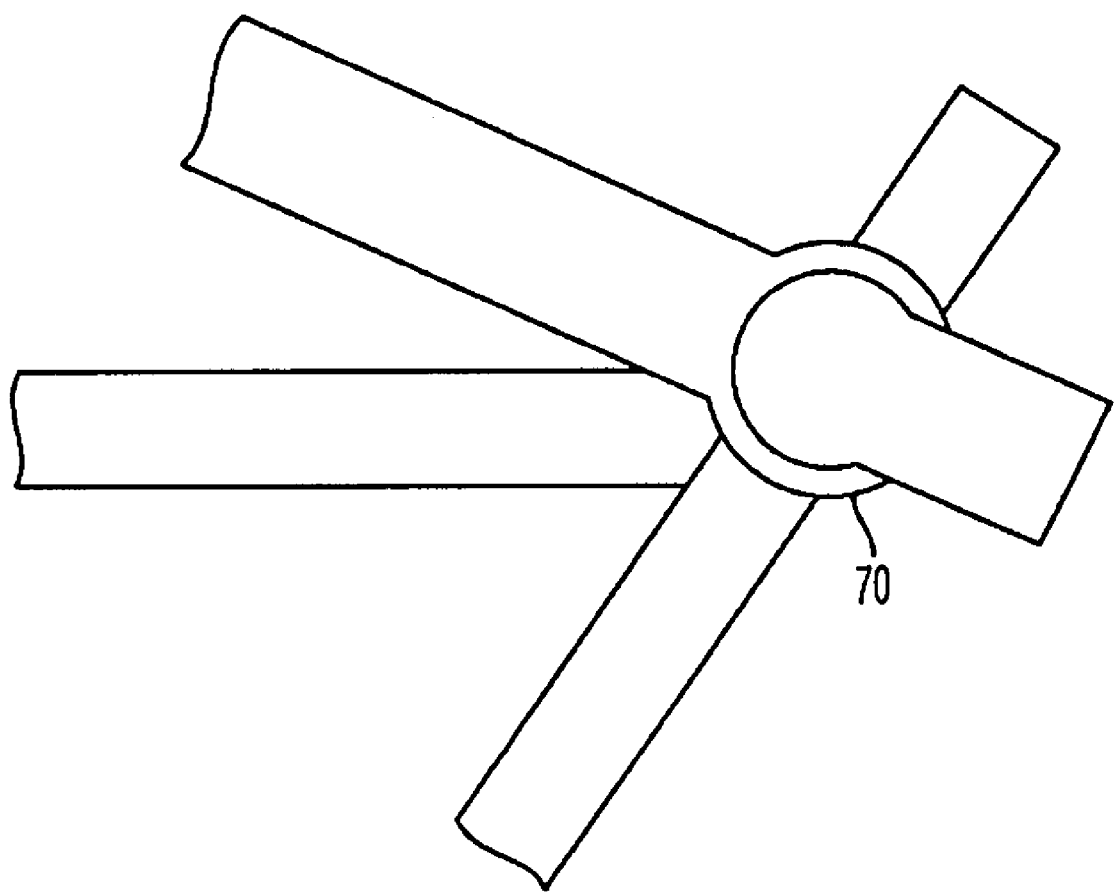
FIG. 17B shows the assembled circuit of FIG. 17A.

A flexible circuit may incorporate more than one flap extension 61 in order that the circuit may be electrically connected to more than one other circuit. FIG. 17A shows a circuit 66 having two flaps 72 and 73 capable of making an electrical connection with two different extension circuits 64 and 65 at connection point 70. When incorporated into an ECG lead wire assembly, circuit 66 and extension circuits 64 and 65 may correspond to the lead wires originating from the above-listed conventional ECG anatomical positions. FIG. 17B shows the completed connection.

Figure 16A:
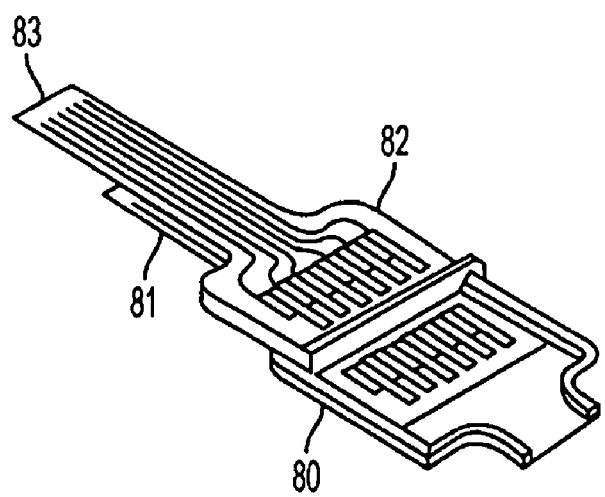
FIG. 16A illustrates a linear connector in the open position for minimizing packaging space.
Figure 16B:
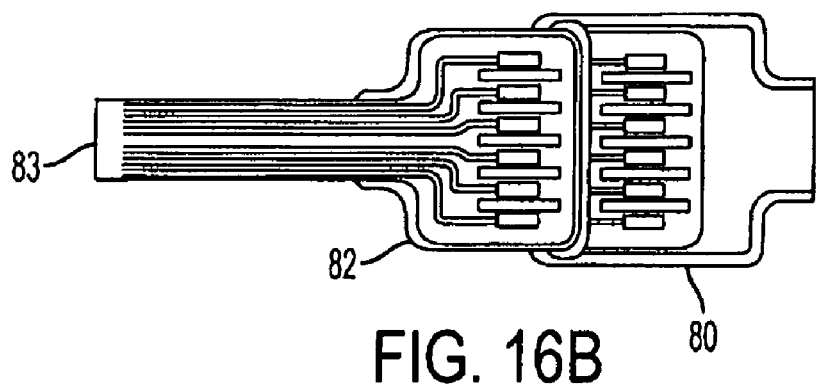
FIG. 16B is a top view of the connector of FIG. 16A.
Figure 16C:
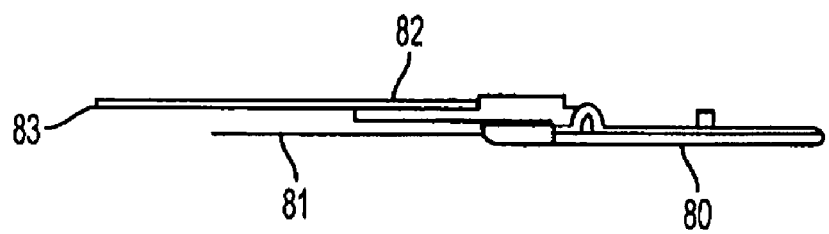
FIG. 16C is a side view of the connector of FIGS. 16A and 16B.
Figure 16D:
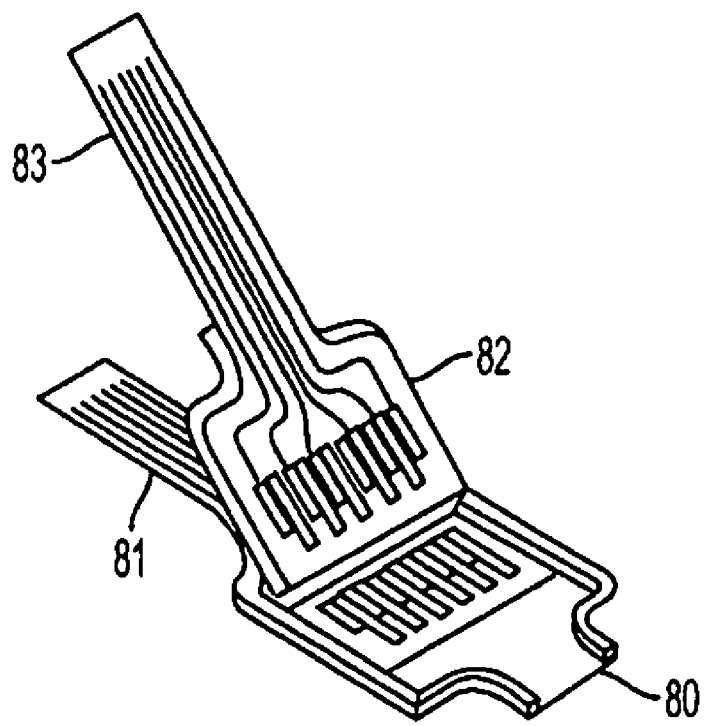
FIG. 16D is an oblique view showing the connector of FIGS. 16A-C as it is being closed.
Figure 16E:
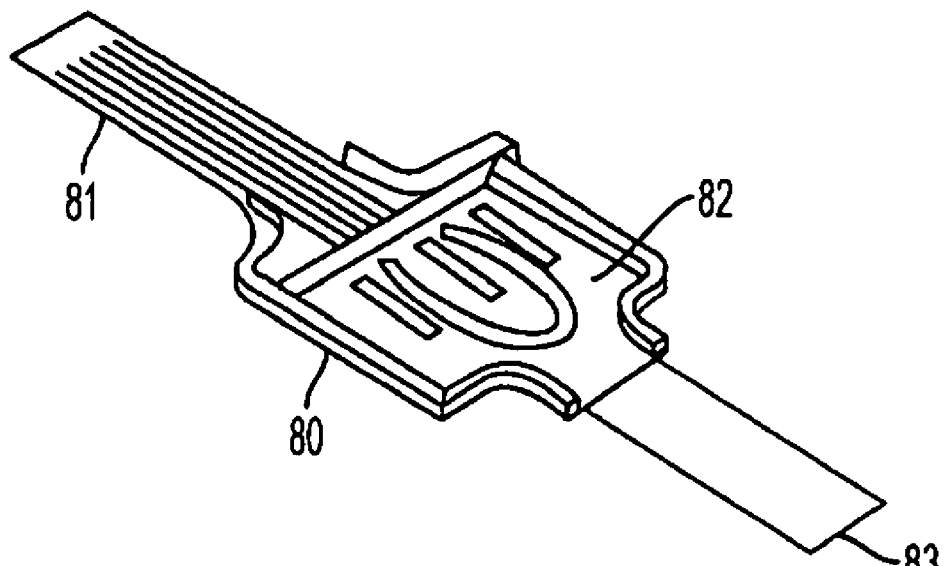
FIG. 16E is the connector of FIGS. 16A-D in the fully closed position.
Figure 16F:
FIG. 16F shows a side view of the connector of FIG. 16A in the open position.
Figure 16G:
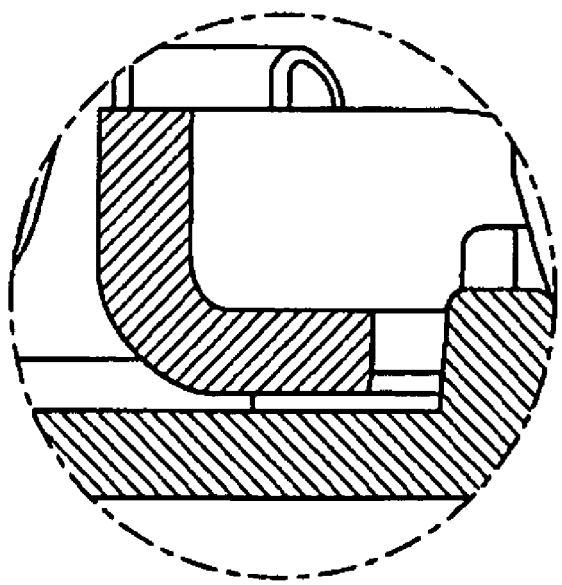
FIG. 16G shows the mechanical mounting mechanism of the connector of FIG. 16A.
Figure 16H:
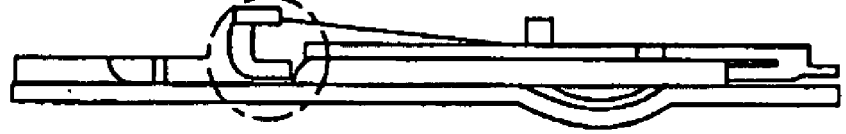
FIG. 16H shows a side view of the connector of FIG. 16A in the closed position.

FIG. 16A shows a linear connector housing for connecting two linear flat circuits. The housing contains a bottom member 80 sized and shaped to receive and retain a first, flat printed circuit 81 in a fixed position. A latching foldable cover 82 sized and shaped to retain a second flat printed circuit 83 in a fixed position is swingingly mounted on the bottom member such that when closed the foldable cover brings the two circuits into electrical contact and serves to fasten them together. FIG. 16B shows a top view of the same connector. FIG. 16C shows the connector in its fully open position for assembly and packaging. FIG. 16D shows the connector in the process of being closed for use. FIG. 16E shows the fully closed connector locked and ready for use. It will be readily apparent to one in the art that by mitering the flat circuits and angling the connector, the connector can also be made to assume a linear shape prior to latching and a non-linear shape after latching.

Figure 18A:
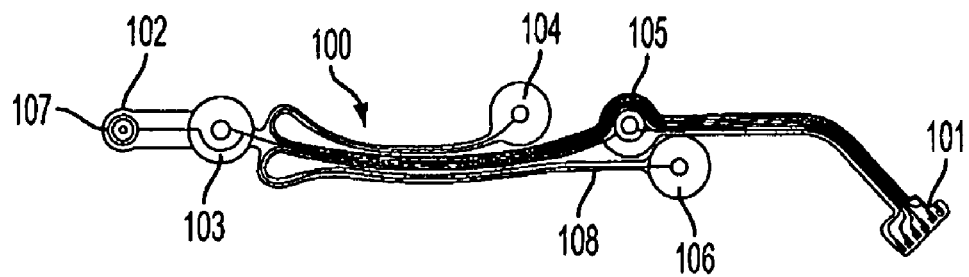
FIG. 18A is a top view of the first half of a six-lead electrocardiogram (ECG) leadwire connector having a linear connector and an articulated connector.
Figure 18B:
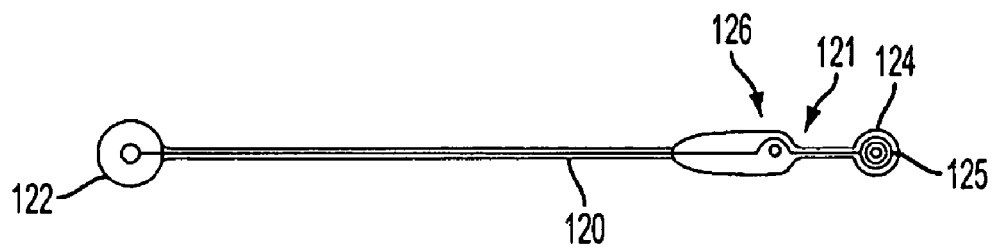
FIG. 18B is a top view of the second half of a six-lead electrocardiogram (ECG) connector having an articulatable connector.
Figure 18C:
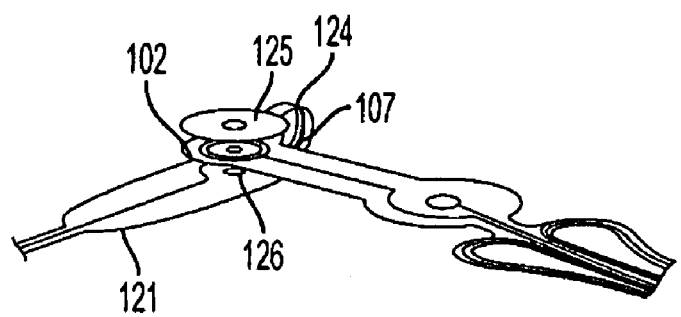
FIG. 18C shows the parts in FIGS. 18A and 18B in position for connection.
Figure 18D:
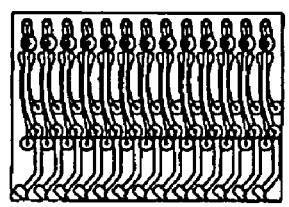
FIG. 18D shows the electrode half of FIG. 18A arranged in an efficient pattern for manufacture.
Figure 18E:
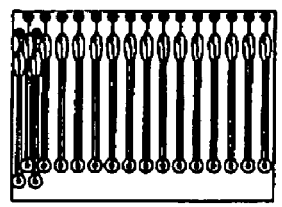
FIG. 18E shows the electrode half of FIG. 18B arranged in an efficient pattern for manufacture.

FIGS. 18A-C illustrate the incorporation of the several embodiments described above with an ECG assembly. FIG. 18A shows the first half of a six-lead leadwire harness 100 having a plurality of discrete electrical traces 108 on a non-conductive substrate. The traces 108 serve to electrically connect, between a linear connector 101 and an articulatable connector 102 having an exposed trace 107, a left arm electrode connector 103, a right leg electrode connector 104, a right arm electrode connector 105, and a reference electrode connector 106. FIG. 18B shows the second half of the leadwire harness 120 having a single electrically conductive trace connecting an articulatable connector 121, with a flap 124 having an exposed trace 125 and a mounting position 126, to a left leg electrode connector 122. FIG. 18C shows the first and second halves of the ECG leadwire assembly in position to be electrically connected via articulatable connectors 102 and 121 at mounting position 126. Articulatable connector 121 is placed on articulatable connector 102 such that the traces are in electrical contact. The full electrical connection is made by folding over flap 124 such that the pivot point is centered over mounting position 126 and secured by mechanically fastening the three layers with a suitable mechanical fastener such as a plastic rivet or snap (not shown). The electrode traces on each half of the electrode halves are covered with a non-conductive substrate, most preferably a fabric such as Sontara®. The connections between the electrode connectors and the ECG electrodes may be made by any means but are most preferably made by exposing the traces such that they make electrical contact with the ECG electrodes and are fastened with a radiolucent elastomeric connector affixed to the top side of the electrode connection.

Figure 19:
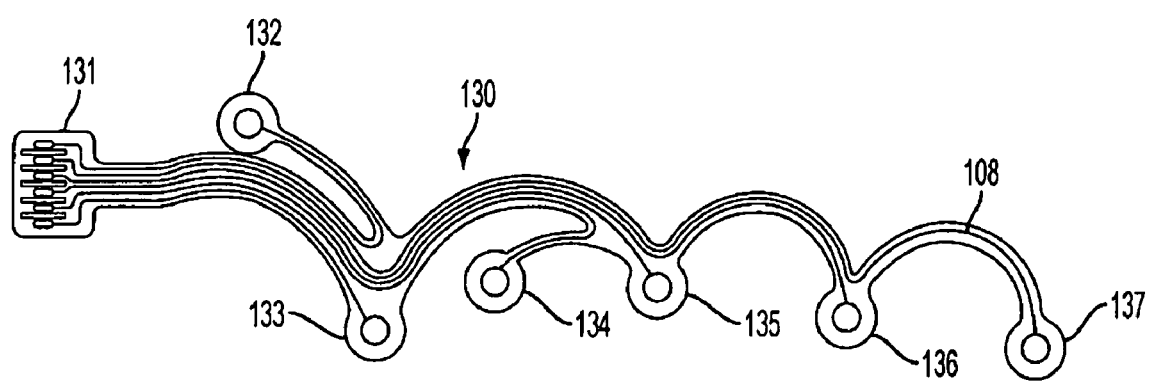
FIG. 19 is a top view of one half of an ECG precordial strip electrode connector having a linear connector.
Figure 20:
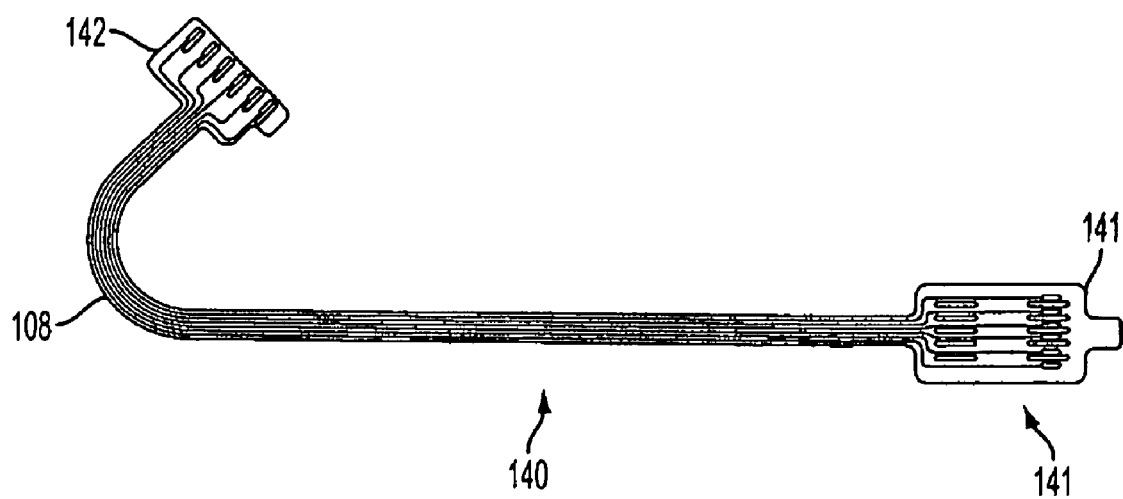
FIG. 20 is a top view of the second half of an ECG precordial electrode connector having a mating linear connector designed to connect to the linear connector shown in FIG. 19 and another connector for connection to an ECG monitor.

FIG. 19 shows an ECG precordial strip electrode connector 130 having a linear connector 131 and connectors for precordial electrodes v1 132, v2 133, v3 134, v4 135, v5 136, and v6 137. The connections between the precordial electrode connectors and the precordial ECG electrodes may be made by any means but are most preferably made by exposing the traces such that they make electrical contact with the ECG electrodes and are fastened with a radiolucent elastomeric connector affixed to the top side of the electrode connection. FIG. 20 shows the second half of precordial electrode connector 140 having a linear connector 141 and another connector 142 for interfacing with an ECG monitor. The linear connector 141 is designed to be mated to the linear connector 131 in such a fashion as described in paragraph [077] of this application. The electrode traces 108 on each half of the precordial electrode halves are covered with a non-conductive substrate, most preferably a fabric such as Sontara®. Conventional means can be used to join components to the printed circuit including hard connectors if desired.

The invention claimed is:

1. A printed circuit connector comprising:
   a first printed circuit having a substrate layer, one or more electrically conductive traces and an insulation layer, wherein the one or more electrically conductive traces are exposed in at least one location on the circuit;
   a second printed circuit having a substrate layer, one or more electrically conductive traces and an insulation layer, wherein the one or more electrically conductive traces are exposed in at least one location on the circuit such that they make direct face-to-face electrical contact with the exposed traces of the first circuit when the circuits are faced insulation layer to insulation layer;
   wherein the first printed circuit and the second printed circuit originate from outside the connector; and
   a means for retaining the first and second circuit in electrical contact.

2. The printed circuit connector of claim 1 wherein the retaining means of the first and second circuit in electrical contact is selected from the following: conductive and non-conductive adhesives, tapes, clamps, housings, conductive fasteners, non-conductive fasteners, interlocking or friction fit between male and female circuit ends.

3. A printed circuit connector comprising:
   a first printed circuit having a substrate layer, one or more electrically conductive traces and an insulation layer;
   a shaped region on the first printed circuit wherein the one or more electrically conductive traces are non-linear and are at least partially exposed;
   a second printed circuit having a substrate layer, one or more electrically conductive traces and an insulation layer, and a shaped region wherein the one or more electrically conductive traces are exposed for electrical connection to the shaped region on the first printed circuit;

wherein the first printed circuit and the second printed circuit originate from outside the connector; and a movable means for retaining the first and second circuits in direct face-to-face electrical contact at the shaped region such that when the first and second circuits are rotated, the one or more traces remain in electrical contact.

4. The connector of claim 3 wherein the shaped region of the first printed circuit is arcuate.

5. The connector of claim 3 where in the shaped region of the second printed circuit is arcuate or linear.

6. The connector of claim 3 wherein the retaining means for the first and second circuits is a mechanical fastener or an external housing.

7. An articulated electrical connector comprised of:

a body comprised of a top surface and a bottom surface, each surface having an aperture;

at least two or more printed circuit ends originating from separate electrical connections, each having an aperture located on its surface;

at least one or more printed circuit traces located on said printed circuit ends that terminate into an annular shape that is concentric about the apertures on said printed circuit ends;

a means for locking said top surface and said bottom surface together such that said at least two or more printed circuit ends are pressed between said top surface and said bottom surface in an overlapping configuration such that the apertures located on the surface of said top surface, said bottom surface, and said at least two or more circuit ends are aligned and form a hole through which a conductive protruding member of a separate electrical conductor may be inserted, such that said at least one or more printed circuit traces on said circuit ends are in direct face-to-face electrical contact wherein said circuit ends may be rotated with respect to one another.

8. The electrical connector according to claim 7 wherein said top surface and said bottom surface of said connector body are flat, identical and composed of plastic.

9. The electrical connector according to claim 7 wherein the apertures located on said top surface, said bottom surface, and said two or more circuit ends are circular.

10. The electrical connector according to claim 7 wherein the apertures are located at the centering axes of said top surface, said bottom surface, and said two or more circuit ends.

11. The electrical connector according to claim 7 wherein said means for locking said top surface and said bottom surface together are comprised of a plurality of protrusions with angled tips along the outer perimeter of the aperture located on said bottom surface such that when the apertures of said top surface and said bottom surface are aligned and pressed together, the protrusions are snap-fitted into the aperture of the adjacent said top surface.

12. The electrical connector according to claim 7 wherein the annular terminating portions of said at least one or more printed circuit traces may be varied in length such that the said circuit ends may be rotated to such a degree that the annular portions are no longer in overlapping electrical contact when the connector body is connected.

13. An articulated electrical connector comprised of:

a body comprised of a flat, non-conductive top surface and an identical bottom surface, each surface having a circular aperture located at its centering axis;

at least two or more circular-shaped printed circuit ends originating from separate electrical connections, each having a circular aperture located at its centering axis;

at least one or more printed circuit traces located on said printed circuit ends that terminate into an annular shape that is concentric about the circular apertures located at the centering axes of said printed circuit ends;

a means for locking said top surface and said bottom surface together such that said at least two or more printed circuit ends are pressed between said top surface and said bottom surface in an overlapping configuration such that the apertures located on the surface of said top surface, said bottom surface, and said at least two or more circuit ends are aligned and form a hole through which a protruding member of a separate electrical conductor may be inserted, such that said at least one or more printed circuit traces on said circuit ends are in direct face-to-face electrical contact wherein said circuit ends may be rotated with respect to one another.

14. The electrical connector according to claim 13 wherein said means for locking said top surface and said bottom surface together are comprised of a plurality of protrusions with angled tips along the outer perimeter of the aperture located on said bottom surface such that when the apertures of said top surface and said bottom surface are aligned and pressed together, the protrusions are snap-fitted into the aperture of the adjacent said top surface.

15. The electrical connector according to claim 13 wherein the annular terminating portions of said one or more printed circuit traces may be varied in length such that the said circuit ends may be rotated to such a degree that the annular portions are no longer in overlapping electrical contact when the connector body is connected.

16. The electrical connector according to claim 13 wherein the conductive protruding member of a separate electrical conductor is a stud-type electrode.

* * * * *